United States Patent [19]
Murray

[11] Patent Number: 5,462,356
[45] Date of Patent: Oct. 31, 1995

[54] BONE AND DENTAL CEMENT METHOD AND PREFORM

[76] Inventor: William M. Murray, 2650 Spring Hill La., Enola, Pa. 17025

[21] Appl. No.: 252,266

[22] Filed: Jun. 1, 1994

[51] Int. Cl.⁶ .............................. B01F 13/06; B01F 3/20
[52] U.S. Cl. ................. 366/348; 366/139; 366/150.1
[58] Field of Search .................... 366/139, 348, 366/150, 154, 167, 168, 169, 241, 242, 244, 602, 255, 256, 267, 1, 2, 3, 6, 10; 494/61; 606/92, 93, 94; 422/99

[56] References Cited

U.S. PATENT DOCUMENTS

| | | | |
|---|---|---|---|
| 3,640,510 | 2/1972 | Lea | 259/108 |
| 4,185,072 | 1/1980 | Puderbaugh et al. | 422/99 |
| 4,277,184 | 7/1981 | Solomon | 366/150 |
| 4,463,875 | 8/1984 | Tepic | 222/82 |
| 4,671,263 | 9/1987 | Draenert | 128/92 |
| 4,721,390 | 1/1988 | Lidgren | 366/139 |
| 4,758,096 | 7/1988 | Gunnarsson | 366/139 |
| 4,787,751 | 11/1988 | Bakels | 366/110 |
| 4,799,801 | 1/1989 | Bruning | 366/255 |
| 4,808,184 | 2/1989 | Tepic | 604/56 |
| 4,854,716 | 8/1989 | Ziemann et al. | 366/139 |
| 4,961,647 | 10/1990 | Coutts et al. | 366/139 |
| 4,973,168 | 11/1990 | Chan | 366/139 |
| 5,015,101 | 5/1991 | Draenert | 366/349 |
| 5,051,482 | 9/1991 | Tepic | 525/309 |
| 5,100,241 | 3/1992 | Chan | 366/139 |
| 5,114,240 | 5/1992 | Kindt-Larsen et al. | 366/129 |
| 5,145,250 | 8/1992 | Planck et al. | 366/8 |
| 5,193,907 | 3/1993 | Faccioli et al. | 366/130 |
| 5,219,897 | 6/1993 | Murray | 523/116 |
| 5,236,971 | 8/1993 | Murray | 523/116 |
| 5,252,301 | 10/1993 | Nilson et al. | 422/225 |
| 5,265,956 | 11/1993 | Nelson et al. | 366/139 |
| 5,336,700 | 8/1994 | Murray | 523/116 |
| 5,348,391 | 9/1994 | Murray | 366/139 |
| 5,368,386 | 11/1994 | Murray | 366/139 |
| 5,395,167 | 3/1995 | Murray | 366/139 |

FOREIGN PATENT DOCUMENTS

| | | |
|---|---|---|
| 4535517 | 4/1970 | Japan. |
| 59-03830 | 9/1984 | Japan. |

OTHER PUBLICATIONS

Howmedica, *The Simplex Enhancement Mixer*, "The Howmedica Experience" Dec., 1985.

Stryker, *High Vacuum Cement Injection System*, "Third Generation Cementing Technique", Jan., 1992.

Zimmer, *Osteobond Vacuum Mixing System*, Jun. 1993.

Depuy, Inc. "Prism Vacuum Mixing Bowl" Flyer (No Date).

*Clinical Orthopedics and Related Research*, "Optimization and Comparison of Three Vacuum Mixing Systems for Porosity Reduction of Simplex P Cement", J. P. Davies & W. H. Harris, May, 1990.

*Primary Examiner*—Robert W. Jenkins
*Attorney, Agent, or Firm*—Thomas Hooker

[57] ABSTRACT

A bone or dental cement mixing method and preform body are disclosed. An elongate rod is inserted into a cement mixing chamber. Cement powder is poured into the mixing chamber and around the rod to form a preform body in the chamber. The rod is moved laterally through the powder to form a channel in the body. Cement liquid is poured on top of the body, flows down the channel and is absorbed into the body. The body and liquid are then physically mixed by a conventional cement mixing device to form a cement with cement liquid uniformly distributed throughout the cement.

40 Claims, 7 Drawing Sheets

BONE AND DENTAL CEMENT METHOD AND PREFORM

FIELD OF THE INVENTION

The invention relates to the mixing of cement used as casting and grouting material in orthopedic and dental applications, and to orthopedic and dental cement performs used in mixing orthopedic and dental cement.

DESCRIPTION OF THE PRIOR ART

Cement used as a casting and grouting material to implant prosthetic devices into live bone is made from a very fine cement powder, typically polymethylmethacrylate (PMMA), mixed with a monomer liquid, typically methylmethacrylate (MMA), to form a flowable bone cement mixture. Physical mixing of the dry cement powder and liquid is required in order to make a flowable cement. It is not sufficient to merely bring the liquid into contact with the cement powder because the liquid will not flow into the powder uniformly. During mixing the monomer liquid should be distributed equally throughout the mixture so that the mixture is uniform and possesses a uniform viscosity, consistent with the manufacturer's specifications.

Bone and dental cements are mixed using pre-packaged amounts of dry PMMA powder and monomer liquid prepared by the manufacturer of the cement. The amounts of powder and liquid are measured to provide a cement mixture having desired properties when the powder and liquid are uniformly mixed together. Failure to mix the liquid and powder together uniformly means that part of the mixture contains an excess of MMA liquid and is runny and part of the mixture contains a deficiency of MMA liquid and is more viscous than desired or, in some cases, retains unwetted dry powder.

Bone cement is conventionally mixed in a closed bone cement mixer. The mixer has a mixing chamber, a lid to close the chamber, and a mixing element movable within the mixing chamber to physically mix the powder PMMA and MMA liquid together to form a flowable bone cement. Cement is mixed by placing the required amounts of PMMA powder and MMA liquid in the mixing chamber, which may be the interior of a syringe cartridge seated in the mixer. A cap is placed on the top of the mixer to close the mixing chamber. The cap supports a mixing element which extends into the mixing chamber. Vacuum is applied to the interior of the chamber to withdraw gas. The mixing element is manually rotated around the chamber for a predetermined amount of time to mix the powder and liquid and form a flowable bone cement.

Prior to mixing, dry PMMA powder is typically poured into the empty mixing chamber and monomer liquid is poured into the chamber on top of the powder. Alternatively, the monomer liquid may be poured into the mixing chamber before PMMA powder is poured into the chamber. When the dry PMMA powder is poured into the mixing chamber, it forms a body having a height. The body is comprised of loosely compacted particles within the chamber. The MMA liquid is on the top of the body of bone cement powder or below the body. In either case, the liquid is not uniformly distributed throughout the height of the powder body and tends to remain at the location where it was poured into the chamber. Before physical mixing of the bone cement there is an excess of liquid at one end of the powder body and a deficiency of liquid at the other end of the powder body. When the liquid is poured on top of the powder, the liquid can form a puddle which seals the top of the powder and prevents underlying air between particles of the bone cement powder from flowing out of the powder.

The problems of uneven MMA liquid distribution just described can be quite significant where the height of the body of bone cement powder is greater than its diameter. This is typically the case where a syringe cylinder is used as a mixing chamber. Because of this problem, some conventional mixers use wide bowl-type mixing chambers rather than narrow syringe cylinders. Cement mixed in a bowl-type mixing chamber must be transferred from the bowl-type chamber to a syringe cylinder for extrusion to a prepared application site. The transfer from the bowl-type mixing chamber to a syringe cylinder takes time, involves loss of cement and, most seriously, includes a likelihood of trapping air inclusions in the body of mixed cement. Air inclusions weaken joints formed by bone cement. After the bone cement powder and liquid are poured into the mixing chamber, the ingredients are physically mixed together by moving the mixing element in the mixing chamber. However, when mixing in a syringe cylinder, the mixing process cannot be expected to produce uniform distribution of monomer along the height of the body. Where there is excess monomer liquid, the mixed bone cement will be less viscous than the manufacturer's standard. Where there is an excess of powder, the resulting mixture will be more viscous than the standard and, indeed, may contain regions where there is no monomer liquid.

It is quite important that monomer liquid be evenly distributed throughout the bone cement mixture. Bone cement with an excess of MMA liquid sets up slowly requiring increased operating room time and the risk of prosthesis displacement during protracted set-up. Such cement also possesses reduced strength. Further, during the increased set-up period there is a risk that blood or other bodily fluid will displace the runny cement from adjacent the formed bone surface at an implant site and thereby weaken fixation between the hardened cement and bone.

Bone cement mixed with a deficiency of MMA liquid has a high viscosity and may be difficult to flow properly to the application site. This cement does not flow readily into the irregularities of a prepared bone surface to form a reliable joint. Further, bone cement with a deficiency of MMA liquid sets up relatively rapidly, reducing the already short amount of time available to the surgeon to perform an implantation procedure.

The implantation of a bone prothesis using a bone cement mixture in which part of the bone cement has an excess of MMA liquid and is relatively runny and part of the bone cement has a deficiency of MMA liquid and is relatively viscous, causes additional problems in the operating room because the surgeon is not able to predict with accuracy the proper length of time for the cement to set and form a joint securing an implanted prosthetic element to a prepared live bone application site. Setting must occur before any stress may be placed on the prosthetic element. Premature stressing of the implanted element will displace the carefully placed element and will impair fixation. For instance, the initial seating of a prosthetic hip ball in the adjacent hip socket stresses the implanted stem on the ball and must be delayed until the bone cement securing the stem in the proximal end of the femur has set. When bone cement is not mixed uniformly, the surgeon must delay seating the ball in the socket for a period of time greater than the specified time for setting the cement. A surgeon implanting a prosthetic element using the bone cement cannot rely on the set-up time specification provided by the bone cement manufacturer. The specification assumes uniform mixing of the cement.

The problems described above are well recognized. A conventional method for achieving greater uniformity of monomer liquid distribution when using a syringe cylinder as a mixing chamber requires pouring cement powder and monomer liquid alternately, in small amounts, into the chamber until the total amounts to be mixed have been poured into the chamber. The powder and liquid are then mixed. While this method can achieve improved uniformity of monomer distribution, it has serious disadvantages. First, it consumes valuable extra time, and the duration of the time consumed results in a mixture which is not homogeneous in terms of the starting time of its mixing and, hence, its setting time. Second, the layering of monomer liquid which results from this method can isolate regions of loosely packed dry powder containing air which will not be effectively removed by application of vacuum during mixing and will form air inclusions in the mixed cement.

SUMMARY OF THE INVENTION

The invention includes a method of mixing bone or dental cement powder and liquid to form a mixture having a uniform consistency with MMA liquid distributed uniformly throughout the mixture; and a preform used in mixing bone cement.

The bone or dental cement powder and liquid are mixed together in a cement mixing chamber by first placing an elongate rod in the chamber with the lower end of the rod resting on the bottom of the chamber and the upper end of the rod extending outwardly of the chamber. The dry cement powder is then poured into the chamber and forms a preform surrounding the lower end of the rod. The rod extends upwardly from the top of the preform of cement powder in the mixing chamber.

After the cement powder has been poured into the chamber to form the preform of dry cement powder, the rod is pivoted back and forth about the lower end to form a distribution channel extending from the bottom of the preform up to the top of the preform. The channel is formed by pushing the dry cement powder particles to either side of the leading sides of the rod and by displacing the particles to either side of the rod as it is moved back and forth. Cement powder particles may fall back into the channel during and after movement of the rod. The cement powder remaining in the channel formed by movement of the rod has a density less than the density of the poured cement powder in the preform filling the mixing chamber. The channel forms a path for flowing MMA monomer liquid down from the top of the preform down through the height of the preform to the bottom of the preform without the monomer liquid forming a puddle on the top of the preform. Since the channel of reduced powder density is formed by displacing powder away or outwardly from the path of the rod, there is a region of increased powder density immediately surrounding the channel. This region of higher density helps to keep most of the MMA flow within the channel.

After the channel has been formed in the preform of dry cement powder, the rod is left motionless in place in the mixing chamber and MMA monomer liquid is poured onto the top of the preform and flows into the channel. The MMA readily flows into and down along the less dense distribution channel, is absorbed into the cement at the sides of the channel and is distributed relatively uniformly along the height of the preform of bone cement powder. The liquid tends to flow rapidly along the channel to the bottom of the preform. Air in the cement powder is displaced upwardly by the liquid and flows out the top of the preform. Because of the channel, MMA will not spread across the entire cross section of the powder at any level. This is important, since wetting of cement across the entire cross section would constitute a barrier to upward flow of air which must be displaced as monomer liquid flows down into the powder. Such a barrier would prevent adequate downward flow of the liquid into the bottom of the powder preform.

As the liquid flows downwardly, the liquid is absorbed into the bone cement powder at the sides of the channel. The greater cross sectional area of the channel adjacent the top of the preform ensures that liquid soaks into the sides of the channel to provide a relatively uniform distribution of liquid along the height of the preform, rather than collecting in a pool at the bottom of the preform.

After the liquid has been flowed into the distribution channel, the elongate rod is withdrawn from the liquid-cement body, the mixing chamber is closed, a mixing element is extended into the chamber along the height of the body and the element is moved throughout the chamber to thoroughly mix together the cement and monomer. Mixing is preferably performed under vacuum in order to remove remaining air trapped between particles of the dry cement powder. Mixing forms a flowable cement mixture in which the MMA liquid is uniformly distributed and which has a uniform viscosity, consistent with the manufacturer's specification.

After mixing, the mixing chamber is opened, the mixer is withdrawn and the mixed bone cement is flowed to an application site. The uniformly mixed bone cement sets up uniformly, consistent with manufacturer's specifications to form secure fixation and grouting.

In a second embodiment of the invention, the rod is a hollow tube providing an air exhaust passage which facilitates flow of air upwardly out of the preform of cement particles as the MMA liquid flows downwardly into the space between the particles. In this way, initial flow of the liquid downward into the cement is facilitated.

In both embodiments of the invention, cement is mixed by forming dry cement powder into a preform having a height, pouring cement liquid on to the top of the preform, flowing the cement liquid down through the height of the preform without physical mixing so that the liquid is substantially uniformly distributed along the height of the preform, and then mechanically mixing the preform so that the bone cement liquid is uniformly distributed throughout the cement to form flowable mixed cement in which the ratio of MMA to PMMA is consistent throughout the cement. The uniform distribution of MMA throughout the PMMA is achieved in two steps. First, the MMA is distributed substantially uniformly throughout the height of the preform. Then, the preform is physically mixed to distribute the MMA laterally and form a body of uniformly mixed cement.

Other objects and features of the invention will become apparent as the description proceeds, especially when taken in conjunction with the accompanying drawings illustrating the invention, of which there are seven sheets and two embodiments.

DESCRIPTION OF THE PREFERRED EMBODIMENTS

FIGS. 1-5 illustrate a first embodiment of the invention.

Figure 1:
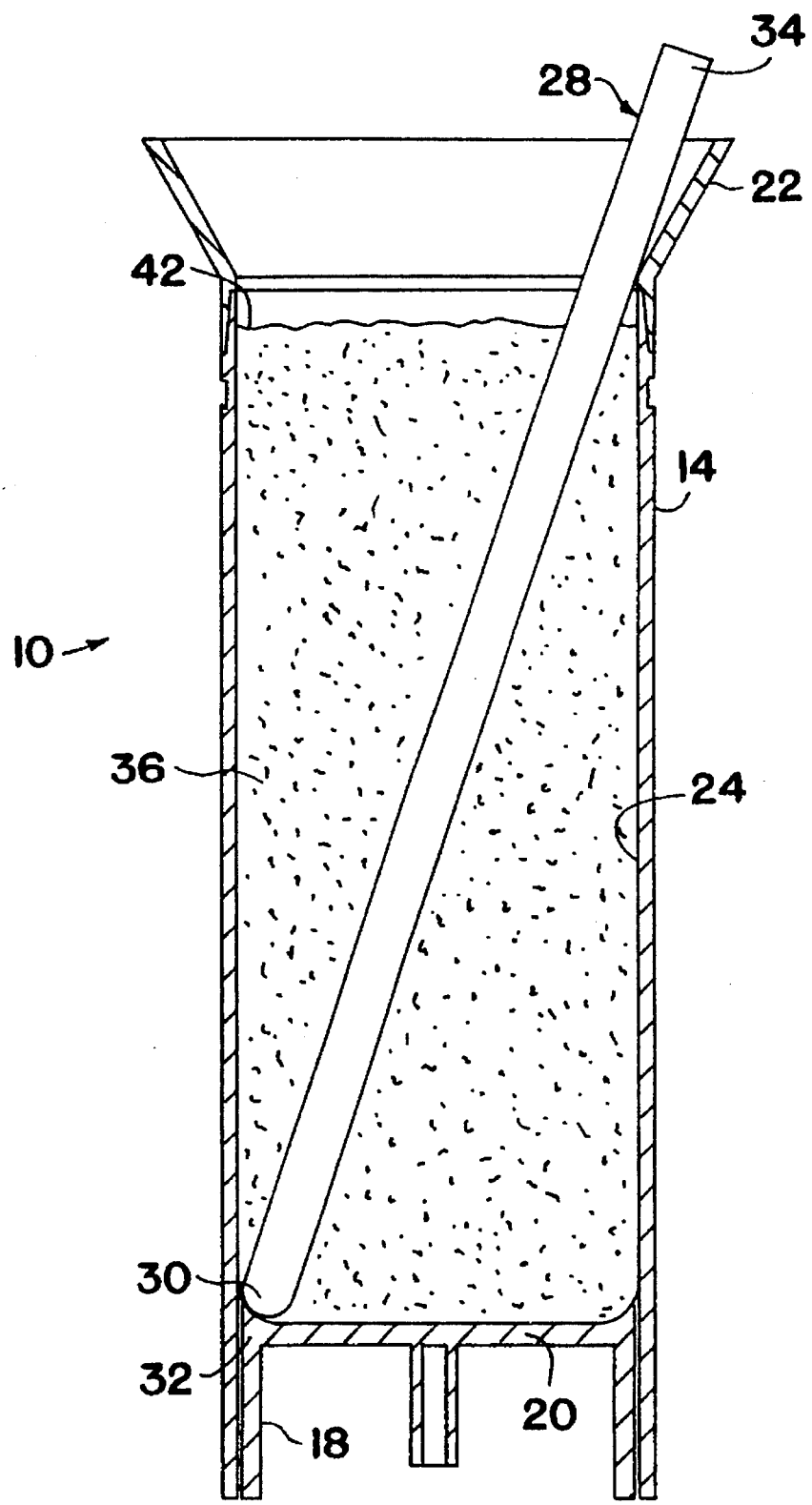
FIG. 1 is a vertical sectional view taken through a cement mixing cartridge showing a rod and preform of cement powder used in mixing bone cement, according to a first embodiment of the invention.
Figure 2:
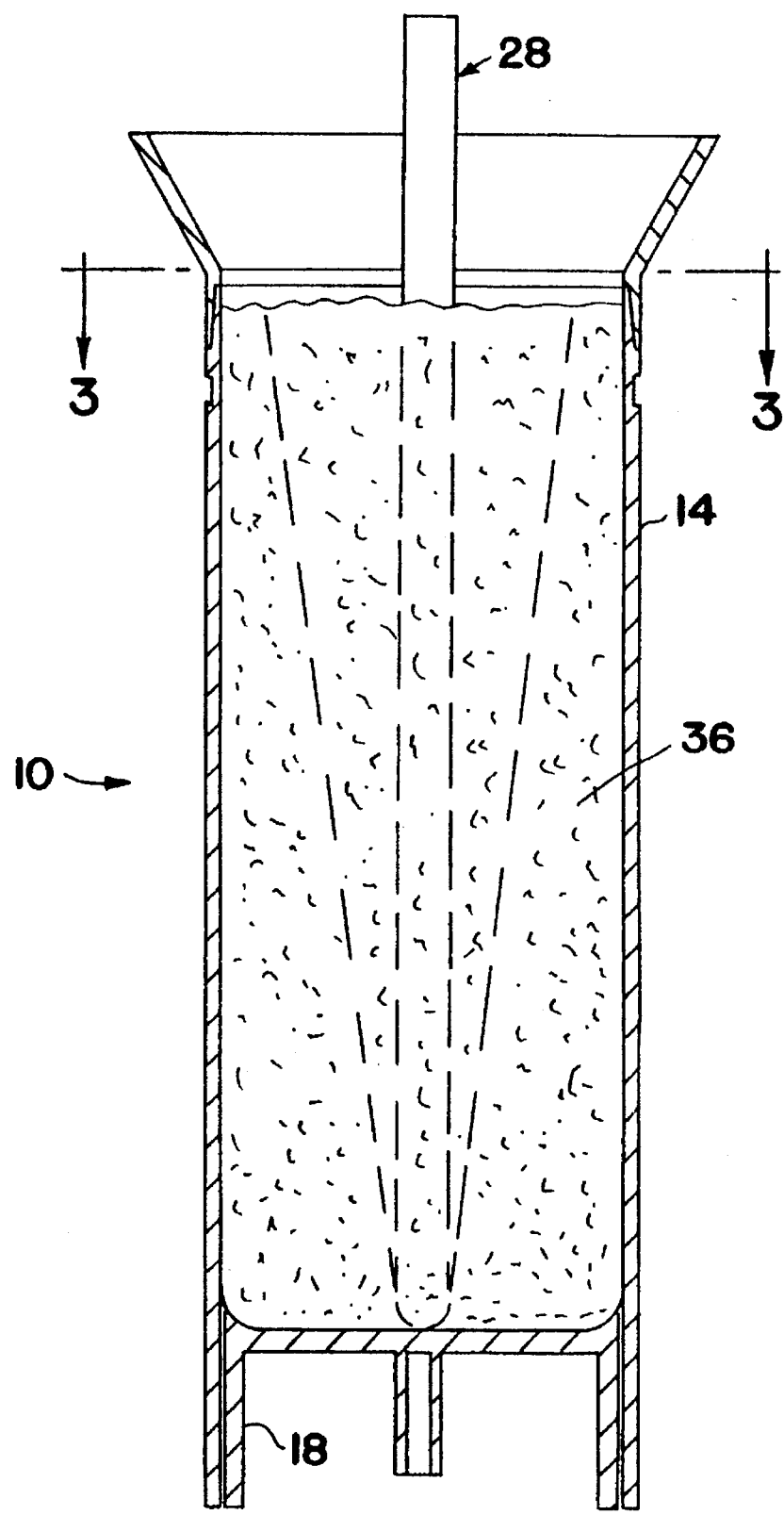
FIG. 2 is a generalized sectional view taken perpendicular to FIG. 1.
Figure 4:
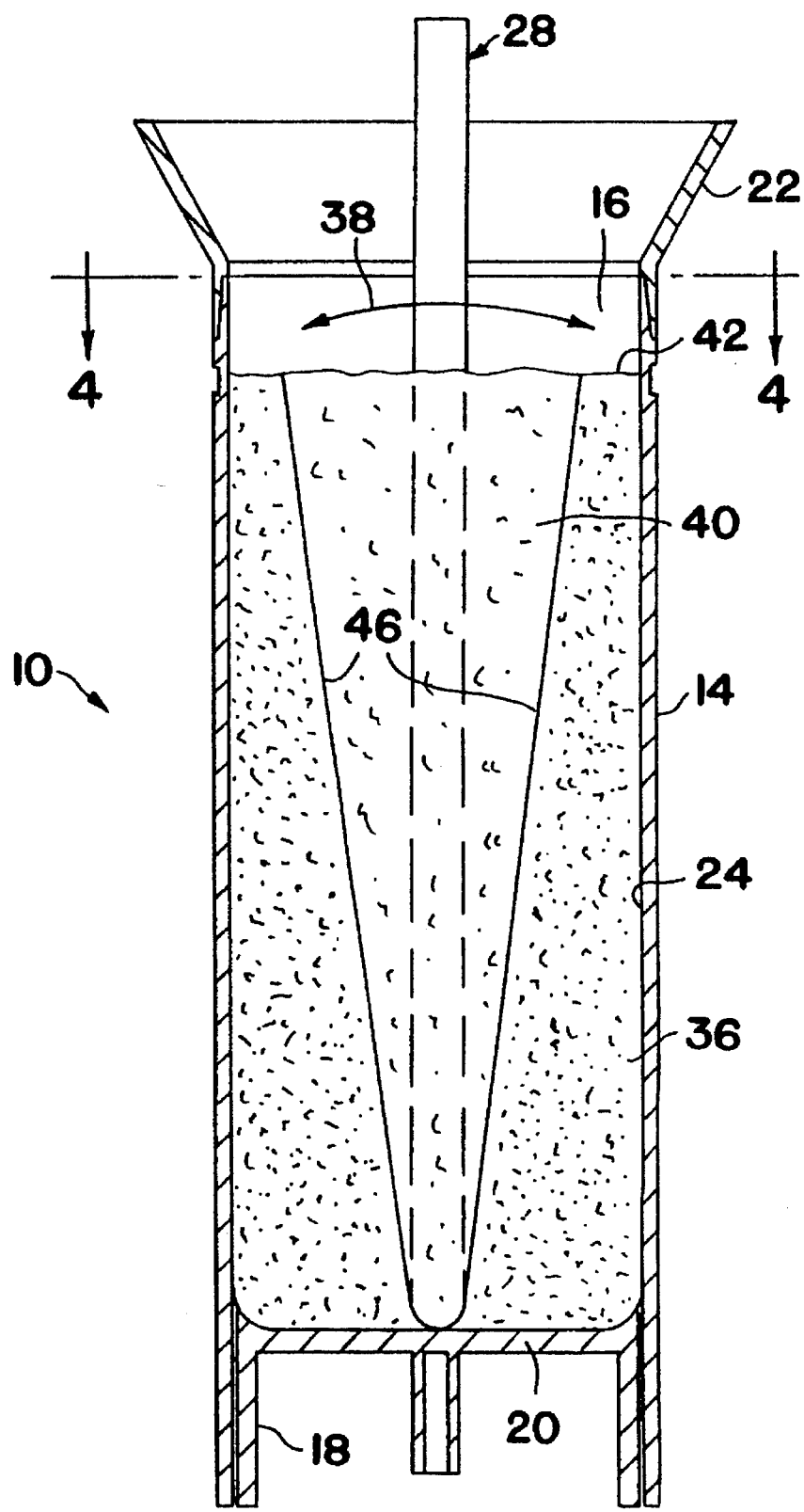
FIG. 4 is a sectional view like FIG. 2 after forming a distribution channel in the preform.
Figure 5:
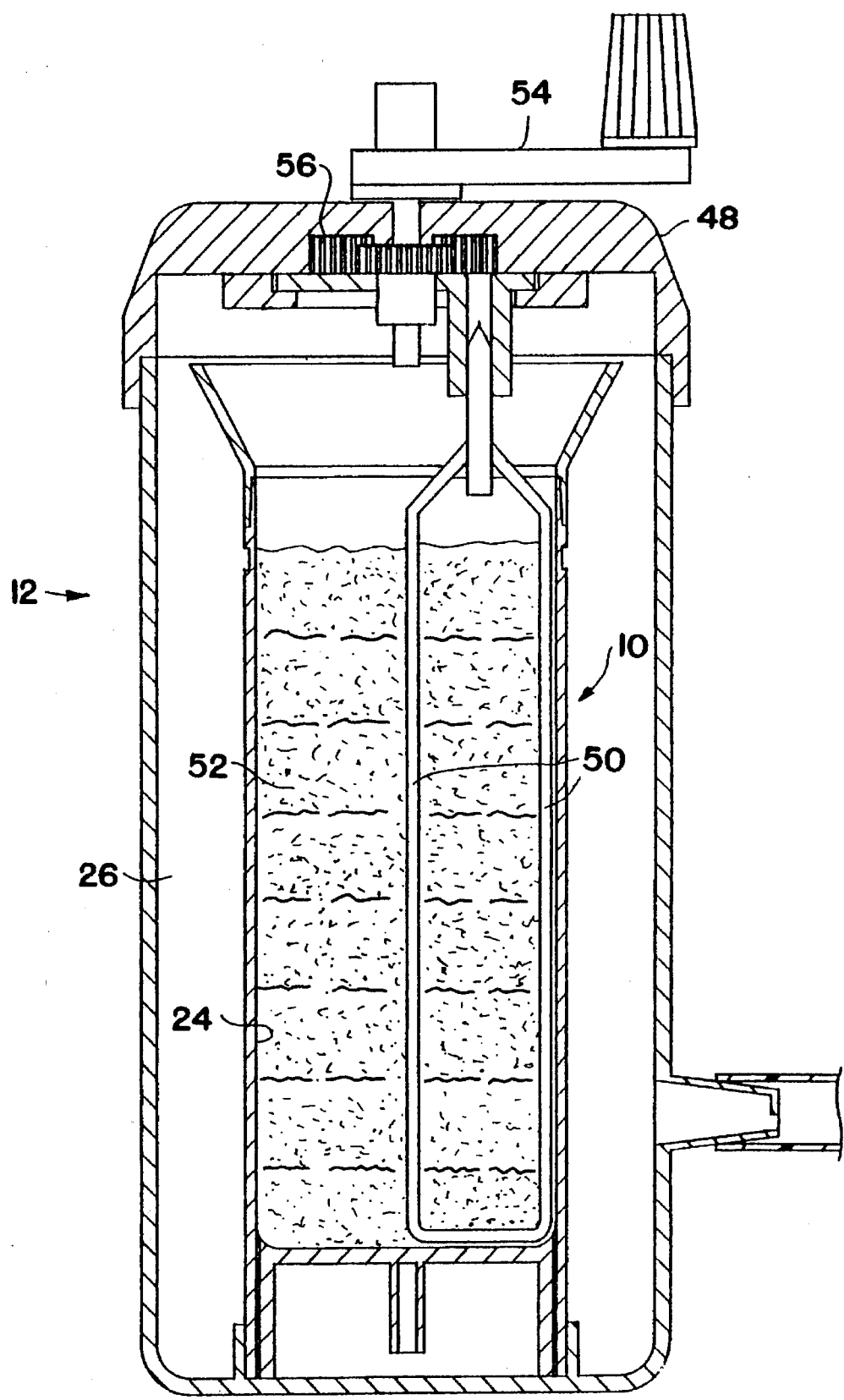
FIG. 5 is a vertical sectional view of a bone cement mixer after mixing.

FIGS. 1, 2 and 4 illustrate a cylindrical syringe cartridge 10 used as a bone cement mixing chamber in mixer 12 shown in FIG. 5. The syringe cartridge includes a cylindrical body 14 having an open upper end 16 and piston 18 forming closed bottom 20. The piston is fitted in the lower end of body 14. An annular lip 32 on the piston seals the lower end of the cartridge. The inner wall of the body and the top on the piston define bone cement mixing chamber 24. Filling funnel 22 is removably mounted on the open upper end of body 14 to facilitate pouring dry powder into mixing chamber 24 and forming a powder preform. Prior to mixing of bone cement, an empty cartridge 10 is seated within the interior 26 of bone cement mixer 12 as shown in FIG. 5.

Acrylic cement is mixed in chamber 24 by first placing an elongate cylindrical rod 28 in the empty chamber in the position shown in FIGS. 1, 2 and 4 with the lower rounded end 30 of the rod engaging the top of piston 18 at the side of the chamber and with the rod angling upwardly through the mixing chamber and resting on the opposite circumferential side of the funnel 22 at the top of the cartridge. The upper free end 34 of the rod extends above funnel 22 to facilitate manual movement of the rod. The rod has a diameter of 0.27 inches.

A premeasured volume of dry acrylic bone cement PMMA powder is poured into chamber 24 over rod 28 to form a preform body 36 of dry, small diameter particles of bone cement powder. A relatively large volume of air is trapped in the preform between the very fine particles of PMMA powder. The density of the PMMA in the preform is relatively uniform along the height of the preform, although the powder at the bottom of a tall preform may be compacted somewhat due to the weight of the powder in the preform. The height of the cylindrical body 36 is greater than its diameter.

Figure 3:
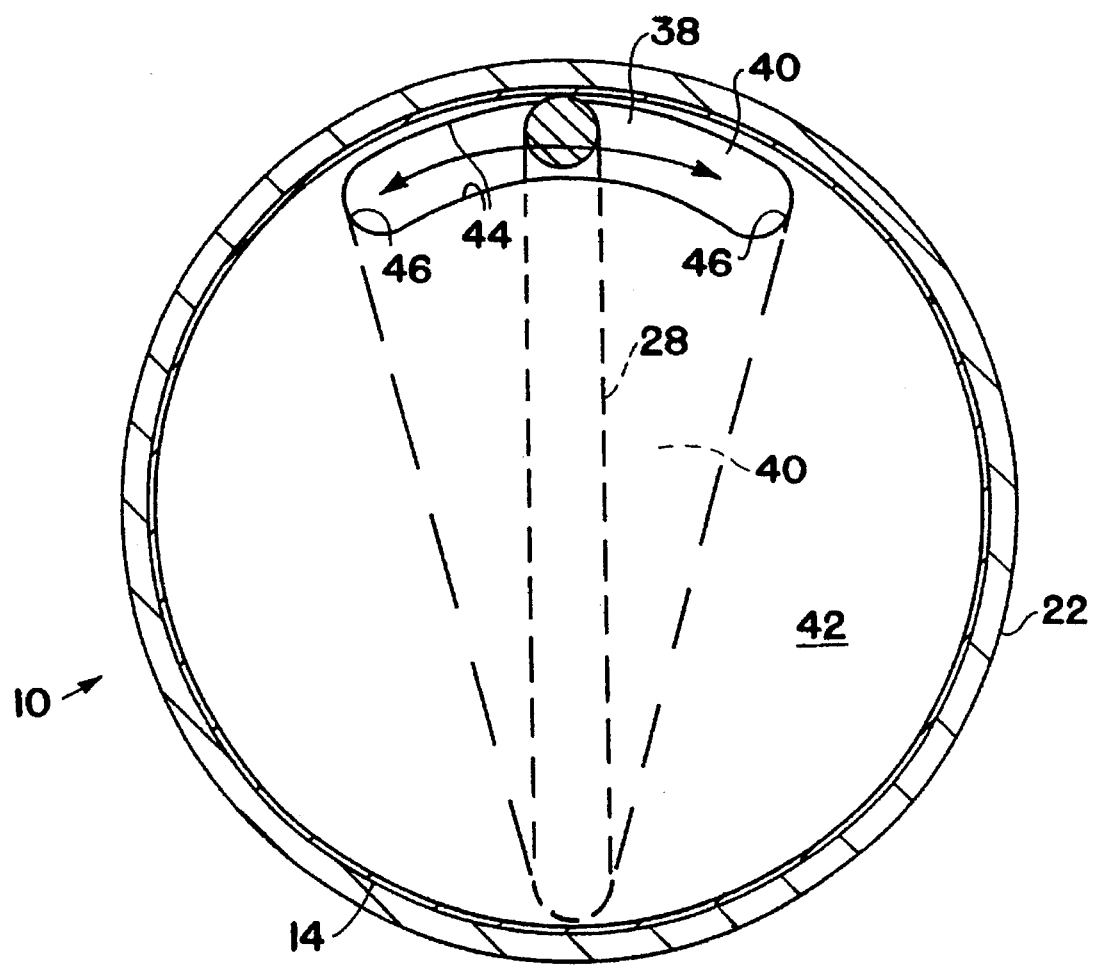
FIG. 3 is a sectional view taken along line 3—3 of FIG. 2.

After the PMMA powder has been poured into the mixing chamber 24 as described, the free end 34 of rod 28 is gripped and the rod is pivoted back and forth about the lower fulcrum end 30, with the upper end of the rod preferably guided in an arc along the interior of funnel 22 as shown in FIGS. 3 and 4. The back and forth movement of the rod indicated by arrow 38 moves the powdered PMMA in the path of the rod away from the rod and forms a vertical monomer flow channel 40 in the preform. The channel extends along the length of the rod from the bottom of the preform 36 up through the top of the preform. Back and forth movement of the rod reduces the density of the cement powder remaining in the channel 40 below the density of the powder in the preform and air voids, free of cement powder, may be formed in the channel. The channel has an upper end opening through the top 42 of preform 36 and is defined by spaced part curved sides 44 and ends 46. The sides 44 are spaced apart a distance equal to the diameter of rod 28, a distance sufficient to permit pouring of acrylic bone cement MMA liquid down the channel. During back and forth movement of the rod some of the powder displaced from the path of movement of the rod typically falls back into the channel, so that its outline is not as clear as shown schematically in the drawings.

After rod 28 has been moved back and forth to form channel 40, the rod is released and the appropriate premeasured volume of MMA liquid required to be mixed with the PMMA powder in the preform is poured onto the top of the preform. The MMA liquid readily flows down the distribution channel 40 without forming a puddle on top of the preform. As the liquid flows down the channel, it is absorbed into the PMMA powder on the sides of the channel so that the MMA liquid is distributed into the powder relatively uniformly along the entire height of the PMMA preform. Air between particles of cement powder in the preform is displaced by the liquid and flows through regions of dry powder upwardly and out of the top of the preform 42.

The channel 40 is tapered and has a maximum cross sectional surface area at the top of the preform and a minimum cross sectional surface area at the bottom of the preform so that the liquid poured into the channel first contacts the upper large surface area and is adsorbed into the dry bone cement powder as it flows down the channel. In this way, the liquid is effectively absorbed into the full height of the preform rather than predominantly flowing down the channel and collecting in a puddle at the bottom of the preform. After the MMA liquid has been poured into the preform of dry PMMA powder to form an unmixed cement-liquid body, rod 28 is removed from the mixing chamber.

Following removal of rod 28, the mixer cap 48 is placed on the top of mixer 12 with mixer arms 50 extending down into the mixing chamber and the unmixed body. Crank 54 on the cap is connected to arms 50 by gear drive 56. The crank is manually rotated to rotate the arms 50 around in the mixing chamber and thoroughly mix the PMMA powder and MMA liquid together to form uniform viscosity bone cement liquid body. The MMA liquid poured into channel 40 is absorbed into the powder at the walls of the channel and is distributed relatively uniformly along the height of body. Powder away from the channel is dry. Mechanical mixing of the body 52 distributes the vertically distributed cement liquid at the channel horizontally throughout the entire body to form a uniformly mixed cement. The MMA monomer liquid is uniformly distributed throughout the mixed cement and the cement is of uniform consistency. Mixing is performed under vacuum to draw away air released from between particles of bone cement powder.

After mixing has been completed, the cap and mixing arms are removed from the mixer. The cartridge and funnel are then removed from the mixer. Uniformly mixed bone cement is dispensed to the operation site by appropriate conventional means.

The bone cement and monomer liquid are thoroughly mixed together in the same proportions throughout each part of the cement, in accordance with the manufacturer's specification. The resultant cement has a uniform consistency and a set time within the manufacturer's specification. Mixing the cement in this way enables the surgeon to perform implantation procedures according to pre-established and known time limits with a resultant strong cement bond securing the prosthetic element in place.

In the drawings, rod 28 is shown with the lower end 30 resting on the bottom of the mixing chamber at one side of the chamber and with the length of the rod extending diagonally across the chamber and resting on the funnel at the opposite side of the chamber. In this way, lateral movement of the rod, as described, forms a tapered distribution channel which extends diagonally across the preform 36 of bone cement powder.

If desired, the rod may be held vertically within the chamber prior to pouring PMMA powder into the chamber and then moved or pivoted laterally to form a vertical distribution channel. The purpose of the channel is to ensure that the MMA liquid poured onto the top of the preform is distributed relatively uniformly along the height of the preform. The channel may be straight or angled as required and need not be tapered, as long as it extends from the top of the preform substantially along the height of the preform.

Figure 6:
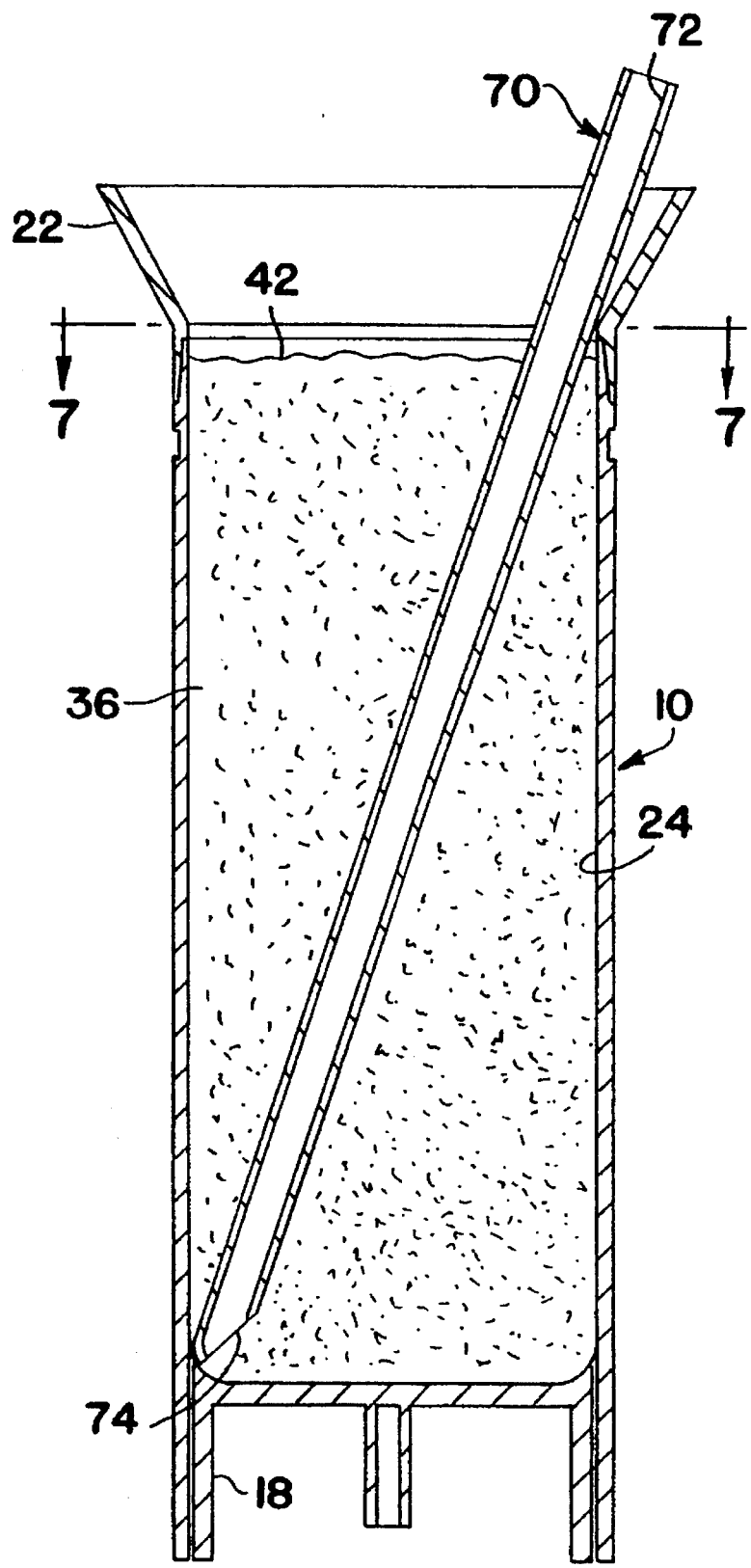
FIG. 6 is a vertical sectional view of a syringe cartridge, rod and powder preform like FIG. 1, according to second embodiment of the invention.
Figure 7:
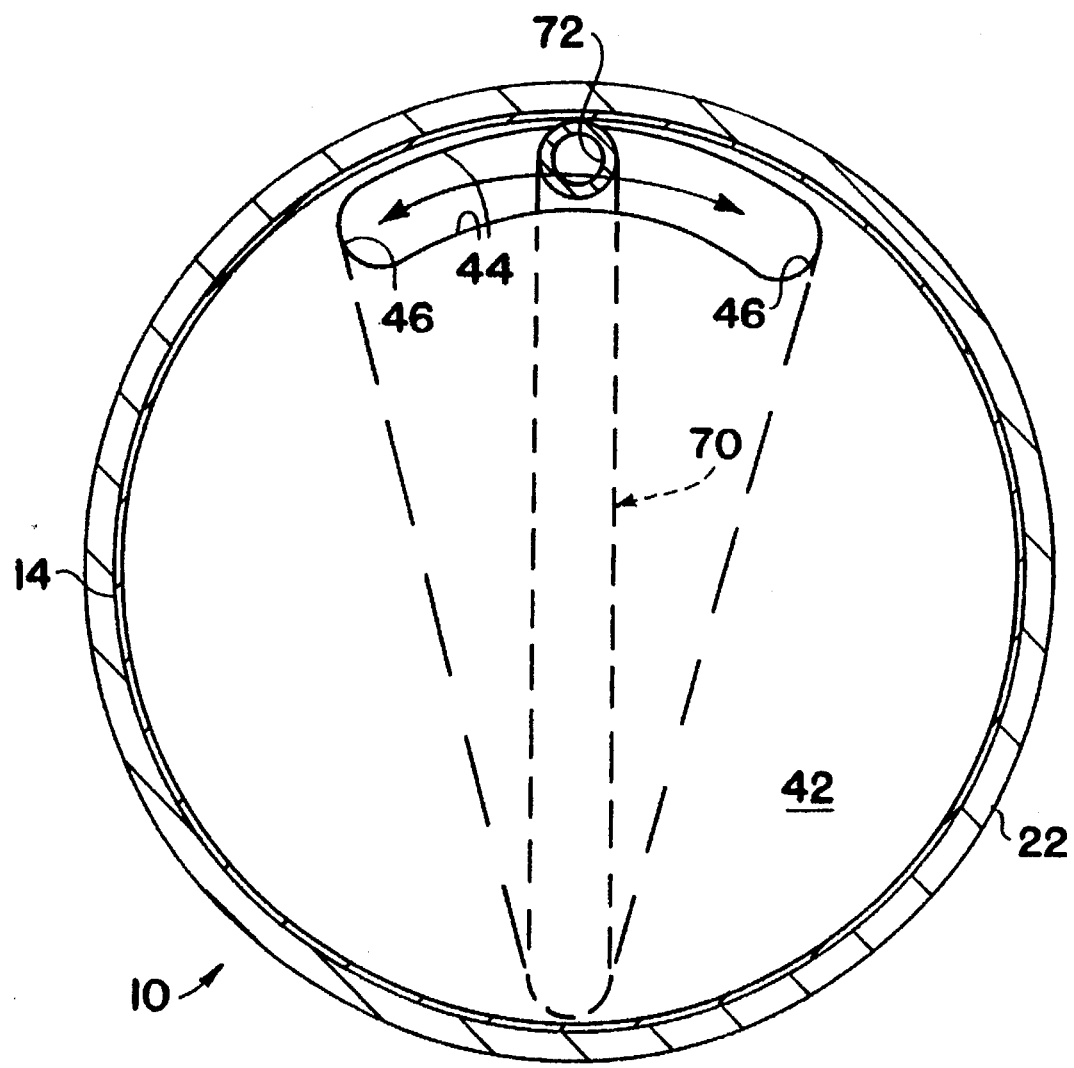
FIG. 7 is a sectional view taken along line 7—7 of FIG. 6.

FIGS. 6 and 7 illustrate a second embodiment of the invention similar to the first embodiment of the invention, except that rod 70 is provided with an elongate central passage 72 extending along the length of the rod. The lower end 74 of the rod is chamfered to provide an inlet which is open when the rod is positioned in mixing chamber 24. The passage 72 extends from opening 74 to the upper end of the rod above funnel 22 to communicate the lower portion of the mixing chamber with the interior of mixer 12 in which cartridge 10 is seated.

Bone cement may be mixed by positioning rod 70 in an empty cartridge 10 with the cartridge seated within mixer 12. Dry powdered bone cement is then poured into the mixing chamber to form preform 36. The lower end of the rod 70 rests against one edge of the piston 18 with the upper end of the rod engaging the opposite side of the funnel. The upper end of the rod is then gripped, as previously described, and moved back and forth to form a monomer liquid flow channel in the preform of dry bone cement powder, as previously described.

After formation of the flow channel, rod 70 is released and the appropriate volume of MMA monomer liquid is poured onto the top of the preform and flows down the channel to the bottom of the preform. MMA liquid is absorbed into the preform as it flows down the channel and is distributed relatively uniformly along the height of the preform in powder adjacent the channel. The remaining powder is dry. The monomer liquid does not form a puddle on the top of the preform.

As the monomer liquid flows into or soaks into the dry cement particles in the preform at the channel, air trapped between the particles is driven out of the preform. Air trapped between particles near the top of the preform flows out of preform top 42. Air trapped in the bottom of the preform flows into the lower open end 74 of rod 70, up through the interior passage 72 and is vented into the interior of the mixer 12 at the top of the cartridge. Direct venting of air from the bottom of the cartridge facilitates the flow of monomer liquid into the dry cement powder.

After liquid monomer has been poured into the channel in preform 36, rod 70 is removed and the cement powder-MMA liquid mixture is mixed as previously described to distribute the liquid uniformly through out the cement.

Monomer liquid may be distributed throughout the height of preform 36 without forming a flow channel in the preform. With the rod 70 in place as shown in FIG. 6, monomer is poured on the top of the preform and flows downwardly through the preform with air trapped in the preform below the monomer liquid vented from preform through passage 72 in rod 70. The liquid is distributed relatively uniformly along the height of the preform. After the monomer liquid has flowed down the preform, the rod is withdrawn and the cement powder-monomer liquid mixture is mixed in mixer 12 as previously described in order to form mixed cement and distribute the liquid uniformly throughout the cement.

When the monomer liquid is initially poured onto the top of preform 36, it may spread to wet the entire surface of the preform but rapidly flows down through the preform as air trapped between particles of bone cement powder in the preform is vented from the lower end of the preform through rod 70.

The invention has been described by reference to mixing bone cement powder and bone cement liquid to make uniform flowable bone cement. The invention may also be used to make uniformly mixed dental cement, acrylic cement and other similar cements.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. The method of making uniformly mixed bone or dental cement from dry cement powder and cement liquid, comprising the steps of:

A) forming a preform body from particles of dry cement powder with air between adjacent particles, the preform having a top, a bottom and a height;

B) pouring cement liquid onto the top of the preform body;

C) flowing the cement liquid into the preform body without physical mixing to distribute the cement liquid substantially uniformly along the height of the preform body;

D) flowing air displaced by cement liquid out of the preform body; and then

E) physically mixing together the cement powder in the preform body and the cement liquid in the preform body to form a flowable cement with cement liquid substantially uniformly distributed throughout the cement.

2. The method of claim 1 including the step of flowing the cement liquid into the preform body without forming a puddle on the body.

3. The method of claim 1 including the steps of forming a channel having sides, the channel extending through the height of the body and open at the top of the body; flowing the cement liquid down the channel; and absorbing the liquid into the sides of the channel.

4. The method of claim 3 including the step of flowing air out of the body through dry cement powder away from the channel.

5. The method of claim 3 including the step of distributing cement liquid laterally throughout the cement powder during step E).

6. The method of claim 3 including the step of forming the channel with a maximum cross sectional area adjacent the top of the body and a reduced cross section below the top of the body.

7. The method of claim 6 including the step of forming the channel with a taper along the height of the body.

8. The method of claim 6 including the step of forming the channel diagonally across the preform body.

9. The method of claim 3 including the step of compacting the powder at the sides of the channel.

10. The method of claim 1 including the steps of placing a rod in a cement mixing chamber with one end of the rod at the bottom of the chamber and with the rod extending upwardly through the chamber; pouring dry cement powder into the chamber over the rod to form the preform body; moving the rod laterally to displace cement powder in the path of the rod and form a bone cement liquid flow channel having sides, said channel extending from the bottom of the preform body to the top of the preform body; flowing cement liquid onto the body and down the channel; and absorbing the liquid into the sides of the channel.

11. The method of claim 10 including the step of withdrawing the rod from the mixing chamber before performing step E).

12. The method of claim 10 including the step of flowing air in the preform body out of the body through a vent passage in the rod.

13. The method of claim 1 including the step of flowing air in the preform body out the top of the body.

14. The method of claim 1 including the step of flowing air in the preform body out a passage having an inlet end at the bottom of the body and an outlet end remote from the body.

15. The method of claim 1 including the step of flowing cement liquid into a first portion of the preform body extending along the height of the preform body without flowing the cement liquid into a dry second portion of the preform body extending from the top of the body along the height of the body and flowing displaced air out of the body through the second portion of the body.

16. The method of claim 1 including the steps of flowing the cement liquid into the top of the body and venting displaced air out from the bottom of the body.

17. The method of claim 16 including the step of venting displaced air out a passage having an inlet end at the bottom of the body.

18. The method of claim 17 including the step of positioning the passage within the body.

19. The method of claim 1 including the step of forming the body with a height greater than the transverse dimension of the body.

20. The method of mixing acrylic cement from dry acrylic cement powder and acrylic cement liquid comprising the steps of:

A) forming a body of dry acrylic cement powder;

B) distributing acrylic cement liquid substantially uniformly throughout the body without mixing; and then C) physically mixing the entire acrylic cement powder and the acrylic cement liquid in the body to form a flowable cement with the cement liquid uniformly distributed throughout the cement.

21. The method of claim 20 including the steps of pouring cement liquid onto one end of the body and distributing the cement liquid throughout the body without puddling.

22. The method of claim 20 wherein the body has a top a height, the step of pouring the cement liquid on the top of the body and distributing the cement liquid down throughout the height of the body.

23. The method of claim 22 including the step of flowing air displaced from the body away from the body during step B).

24. The method of claim 23 including the step of flowing displaced air away from the body through the top of the body.

25. The method of claim 23 wherein the body has a bottom opposite said top and including the step of flowing displaced air from the body through a passage having an inlet end at the bottom of the body and an outlet end remote from the body.

26. The method of claim 20 wherein the body has a top and a height, including the steps of forming a liquid flow channel in the body, said channel having sides, the channel extending along the height of the body and having an open end at the top of the body; flowing cement liquid into the channel; and absorbing the cement liquid into the cement powder at the sides of the channel.

27. The method of claim 20 including the steps of placing an elongate rod having lower end in a cement mixing chamber having a bottom with the lower end of the rod at the bottom of the chamber; pouring dry cement powder into the chamber so that the powder surrounds the lower end of the rod; moving the rod laterally in the chamber to form a flow channel extending from the bottom of the body to the top of the body; pouring cement liquid into the channel and flowing the liquid cement from the channel into the body.

28. The method of claim 27 including the steps of moving some particles into the channel so that the density of cement powder in the channel is less than the density of the cement powder particles in the body.

29. The method of claim 28 wherein the channel has sides and including the step of compacting cement powder at the sides of the channel.

30. The method of claim 29 including the step of spacing opposed sides of the channel apart a distance of about 0.27 inches.

31. The combination of a bone or dental cement mixing chamber, a preform body of poured dry cement powder in the bottom of the mixing chamber, the body having a top, a bottom and a height and comprising dry fine cement particles and air entrapped between the particles; and a cement liquid flow channel formed in the body, the channel opening at the top of the body and extending downwardly through the height of the body to the bottom of the body.

32. The combination of claim 31 including cement powder in the channel and wherein the density of the cement in the body is greater than the density of the cement in the channel.

33. The combination of claim 31 wherein the channel has a maximum cross sectional area at the top of the body and is tapered.

34. The combination of claim 31 wherein the channel has sides and the cement powder is compacted at the sides of the channel.

35. The combination of claim 31 including cement liquid absorbed into the cement powder at the sides of the channel only, said cement liquid being substantially uniformly distributed along the height of the body.

36. The combination of claim 31 including a rod in the channel extending from the bottom of the mixing chamber through the top of the body, said channel being formed by movement of the rod.

37. The combination of claim 31 including an air vent passage having an inlet end at the bottom of the body and a discharge end remote from the body.

38. The combination of claim 37 including a rod in the mixing chamber and wherein said passage extends through said rod.

39. The combination of a bone or dental cement mixing chamber, a preform body of poured dry cement powder in the bottom of the mixing chamber, the body having a top, a bottom and a height and comprising dry, fine cement particles and air entrapped between the particles, and an air vent passage having an inlet end at the bottom of the body and a discharge end remote from the body.

40. The combination of claim 39 including a rod in the mixing chamber and wherein said passage extends through said rod.

* * * * *